United States Patent [19]

Gettings et al.

[11] Patent Number: 5,013,459
[45] Date of Patent: May 7, 1991

[54] OPTHALMIC FLUID DISPENSING METHOD

[75] Inventors: Richard L. Gettings, Freeland; William C. White, Midland, both of Mich.

[73] Assignee: Dow Corning Corporation, Midland, Mich.

[21] Appl. No.: 433,817

[22] Filed: Nov. 9, 1989

[51] Int. Cl.$^5$ .............................................. C02F 1/50
[52] U.S. Cl. .................................. 210/764; 210/282; 210/469; 210/501; 210/505; 210/510.1; 514/840
[58] Field of Search ............... 210/668, 679, 755, 764, 210/807, 192, 282, 291, 251, 416.1, 416.2, 416.3, 466–469, 501, 504, 505, 510.1; 55/274; 514/63, 839, 840

[56] References Cited

U.S. PATENT DOCUMENTS

| | | | |
|---|---|---|---|
| 3,560,385 | 2/1971 | Roth | 252/49.6 |
| 3,730,701 | 5/1973 | Isquith et al. | 71/67 |
| 3,794,736 | 2/1974 | Abbott et al. | 424/78 |
| 3,817,739 | 6/1974 | Abbott et al. | 71/67 |
| 3,860,709 | 1/1975 | Abbott et al. | 424/184 |
| 3,865,728 | 2/1975 | Abbott et al. | 210/501 |
| 3,951,798 | 4/1976 | Haldopoulos | 210/469 |
| 4,005,028 | 1/1977 | Heckert | 252/99 |
| 4,161,518 | 1/1979 | Wen et al. | 424/52 |
| 4,259,103 | 3/1981 | Malek et al. | 71/67 |
| 4,282,366 | 8/1981 | Eudy | 556/413 |
| 4,371,577 | 2/1983 | Sato et al. | 428/96 |
| 4,394,378 | 7/1983 | Klein | 424/184 |
| 4,406,892 | 9/1983 | Eudy | 424/184 |
| 4,467,013 | 8/1984 | Baldwin | 428/289 |
| 4,472,327 | 9/1984 | Neefe | 264/1.9 |
| 4,504,541 | 3/1985 | Yasuda et al. | 428/264 |
| 4,555,347 | 11/1985 | O'Dowd et al. | 210/704 |
| 4,557,854 | 12/1985 | Plueddemann | 252/174 |
| 4,564,456 | 1/1986 | Homan | 210/698 |
| 4,567,039 | 1/1986 | Stadnick | 132/70 |
| 4,614,675 | 9/1986 | Ona et al. | 427/387 |
| 4,615,882 | 10/1986 | Stockel | 514/63 |
| 4,631,273 | 12/1986 | Blehm et al. | 514/29 |
| 4,631,297 | 12/1986 | Battice et al. | 521/78 |
| 4,648,978 | 3/1987 | Makinen et al. | 210/762 |
| 4,682,992 | 7/1987 | Fuchs | 55/279 |
| 4,721,511 | 1/1988 | Kupits | 8/188 |
| 4,772,593 | 9/1988 | Whalen et al. | 514/63 |
| 4,781,974 | 11/1988 | Bouchette | 428/288 |
| 4,822,667 | 4/1989 | Goad et al. | 428/265 |
| 4,835,019 | 5/1989 | White et al. | 427/387 |

FOREIGN PATENT DOCUMENTS

| | | |
|---|---|---|
| 1217004 | 1/1987 | Canada . |
| WO86/01457 | 1/1987 | PCT Int'l Appl. . |
| 1386876 | 3/1975 | United Kingdom . |
| 1433303 | 4/1976 | United Kingdom . |

OTHER PUBLICATIONS

Applied Microbiology, vol. 24, No. 6, Dec. 1972, A. J. Isquith et al., "Surface Bonded Antimicrobial Activity of an Organosilicon Quaternary Ammonium Chloride".

Primary Examiner—Tom Wyse
Attorney, Agent, or Firm—Jim L. DeCesare

[57] ABSTRACT

A method and device for dispensing an aqueous fluid which is desired to be maintained in a sterile condition. The method includes storing a quantity of aqueous fluid such as ophthalmic saline solution in a reservoir within a portable container having an outlet. A porous filter medium is arranged within the container adjacent the outlet, and the aqueous ophthalmic fluid is caused to pass from the reservoir through the porous medium and to the outlet. The porous medium has covalently bonded thereto an antimicrobially effective amount of an organosilicon quaternary ammonium compound which is an organosilane. The organosilane can also be bonded to the inner and outer surfaces of the portable container.

40 Claims, 1 Drawing Sheet

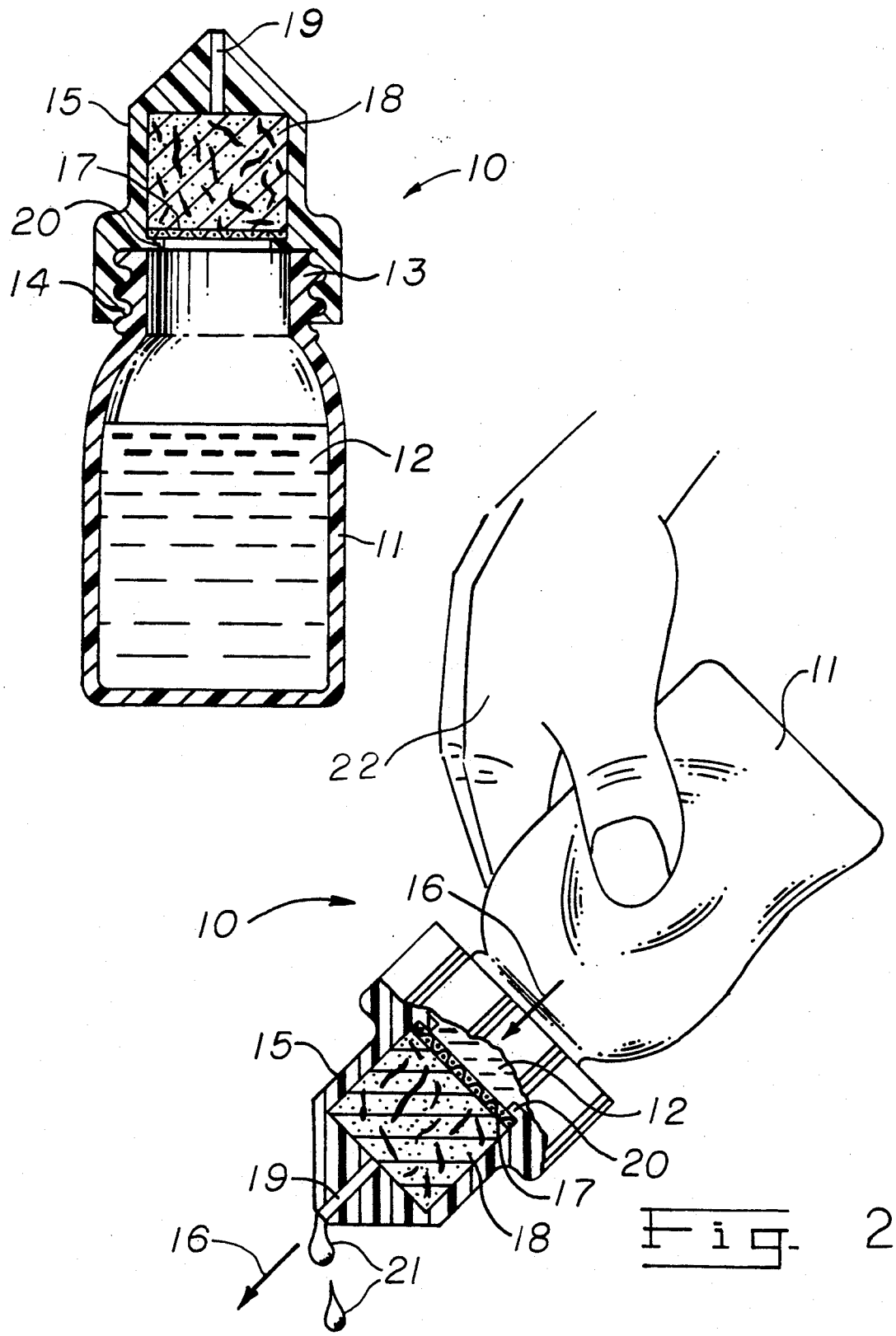

OPTHALMIC FLUID DISPENSING METHOD

BACKGROUND OF THE INVENTION

This invention relates to a method of dispensing an opthalmic fluid from a portable container which includes a porous filter medium having bonded thereto an antimicrobial agent in order to eliminate contamination by microbial growth.

An antimicrobial is an agent that destroys or inhibits the growth of microorganisms. The major classes of microorganisms are bacteria, fungi including mold and mildew, yeasts, and algae. Microorganisms can be found in the air, the waters, the human body, soil, wastes, and on all surfaces. The organisms are deposited from the air, food and drink spills, dust, dirt and tracked in soil, and from human excreta such as sweat, urine, and feces. Organisms grow and multiply when there is available a nutrient source of food such as dirt, organic or inorganic material, and living tissue. For growth and multiplication, organisms also require warm temperatures, and moisture. When these conditions exist, microorganisms thrive and flourish. Microbial growth, however, leads to many problems such as unpleasant odors ranging from stale to musty and mildew-like, to putrid and foul smelling, resembling ammonia. The growths also produce unsightly stains, discoloration, and deterioration of many surfaces and materials in which they come into contact. A more serious disadvantage of microbial growth is the production of pathogenic microorganisms, germs, their metabolic products and their somatic and reproductive cell parts, which contribute to the spread of disease, infection, and disorders.

Antimicrobial agents are chemical compositions that are used to prevent such microbiological contaminations by inhibiting, killing and/or removing them and neutralizing their effects of deterioration, defacement, odor, disease or other negative effects. Particular areas of application of antimicrobial agents and compositions are, for example, cosmetics, disinfectants, sanitizers, wood preservation, food, animal feed, cooling water, metalworking fluids, hospital and medical uses, plastics and resins, petroleum, pulp and paper, textiles, latex, adhesives, leather and hides, and paint slurries. In the area of medical applications, antimicrobials are often used as powders, in lotions, creams, ointments and/or delivered in a variety of solvents or directly as over-the-counter or ethical drugs to alleviate, mediate, cure and/or protect people or other animals from disease or cosmetic conditions. Of the diverse categories of antimicrobial agents and compositions, quaternary ammonium compounds represent one of the largest of the classes of antimicrobial agents in use. At low concentrations, quaternary ammonium type antimicrobial agents are bacteriostatic, fungistatic, algistatic, sporostatic, and tuberculostatic. At medium concentrations they are bactericidal, fungicidal, algicidal, and viricidal against lipophilic viruses. Organosilicon quaternary ammonium salt compounds are well known as exemplified by U.S. Pat. No. 3,560,385, issued Feb. 2, 1971, and the use of such compounds as antimicrobial agents is taught, for example, in a wide variety of patents such as U.S. Pat. Nos. 3,730,701, issued May 1, 1973, and 3,817,739, issued June 8, 1974, where the compounds are used to inhibit algae; 3,794,736, issued Feb. 26, 1974, and 3,860,709, issued Jan. 14, 1975, where they are employed for sterilizing or disinfecting a variety of surfaces and instruments; and 3,865,728, issued Feb. 11, 1975, where the compounds are used to treat aquarium filters. PCT Application No. 8601457, published Jan. 15, 1987, teaches that microorganisms on multi-cellular plants and fruit can be killed by the application thereto of an aqueous mixture of a surfactant and an organosilicon quaternary ammonium compound. U.S. Pat. No. 4,564,456, issued Jan. 14, 1986, discloses organosilanes as anti-scale agents in water systems. In a particular application of an antimicrobial organosilicon quaternary ammonium compound, a paper substrate is rendered resistant to the growth of microorganisms in U.S. Pat. No. 4,282,366, issued Aug. 4, 1981. In U.S. Pat. No. 4,504,541, issued Mar. 12, 1985, an antimicrobial fabric is disclosed which is resistant to discoloration and yellowing by treatment of the fabric with a quaternary ammonium base containing an organosilicon compound. U.S. Pat. No. 4,781,974, issued Nov. 1, 1988, relates to wet wiper towelettes having an antimicrobial agent substantive to the fibers of the web and being an organosilicon quaternary ammonium compound. In U.S. Pat. No. 4,467,013, issued Aug. 21, 1984, such compounds are disclosed to be useful in surgical drapes, gowns, dressings, and bandages. Organosilicon quaternary ammonium compounds have been employed in carpets, in U.S. Pat. No. 4,371,577, issued Feb. 1, 1983; applied to walls, added to paints, and sprayed into shoes, in U.S. Pat. No. 4,394,378, issued July 19, 1983; applied to polyethylene surfaces and used in pillow ticking in U.S. Pat. No. 4,721,511, issued Jan. 26, 1988; in flexible polyurethane foams of fine-celled, soft, resilient articles of manufacture in U.S. Pat. No. 4,631,297, issued Dec. 23, 1986; and mixed with a surfactant in British Pat. No. 1,386,876, of Mar. 12, 1975. Some general, more domestic type applications of these compounds, has included their use in a dentifrice as in U.S. Pat. No. 4,161,518 issued July 17, 1979; in a novel laundry detergent in U.S. Pat. No. 4,557,854, issued Dec. 10, 1985; as a hair conditioner in U.S. Pat. No. 4,567,039, issued Jan. 28, 1986; and in a soft contact lens disinfectant solution in U.S. Pat. No. 4,615,882, issued Oct. 7, 1986. In U.S. Pat. No. 4,614,675, issued Sept. 30, 1986, properties can be influenced by mixing the organosilicon quaternary ammonium compounds with certain siloxanes.

Other typical uses of organosilicon quaternary ammonium compounds in accordance with the prior art can be seen from U.S. Pat. Nos. 4,005,028, issued on Jan. 25, 1977, and relating to hard surface rinse aids and detergents. Contact lenses are treated with an organosilane in U.S. Pat. No. 4,472,327, issued Sept. 18, 1984. In U.S. Pat. No. 4,682,992, issued July 28, 1987, glass spheres are treated with the compounds and employed as filters. The compounds are used to treat swine dysentery in U.S. Pat. No. 4,772,593, issued Sept. 20, 1988; applied to a polyester fabric in U.S. Pat. No. 4,822,667, issued Apr. 18, 1989; and adhered to a polyamide filament in U.S. Pat. No. 4,835,019, issued May 30, 1989. In Canadian Patent No. 1,217,004, granted Jan. 27, 1987, organosilane quaternary ammonium compounds are formulated into bleaches that are applied to hard surfaces such as bath tubs, wash basins, toilets, drains, and ceramic tile floors.

Among the numerous attempts to alleviate the problems of microorganisms on surfaces have involved the use of soaps, detergents, and surface cleaners. The treatments, however, have for the most part included an unbound category of antimicrobial which is not actually bonded to the surface sought to be treated, and therefore is consumed by the microorganisms, with the result that the unbound antimicrobial is depleted and washed away during routine cleansing. As this diffusion continues, the concentration of the active ingredient becomes diluted below effective levels, with the result that the microorganisms sought to be inhibited, adapt and build up a tolerance, becoming immune to what was once an effective treatment dose. Such unbound diffusible antimicrobials have therefore been found to be limited in their ability to offer broad spectrum control of microorganisms, in contrast to the bound type of antimicrobial which remains chemically attached to the surface to which it is applied providing for a surface that prevents recolonization by the microflora associated therewith. Diffusing types of antimicrobials also often suffer from the propensity to transfer percutaneously, giving rise to sensitization and irritation immunological responses, and raising serious questions as to their ultimate fate within the body and body systems.

The "unbound" antimicrobials of the prior art are not the equivalent of the "bound" antimicrobial organosilane of the present invention because the unbound antimicrobials do not perform substantially the same function, in substantially the same way, to produce substantially the same results, as do the bound silanes of the present invention. The function differs because the bound antimicrobial is permanent whereas the unbound types are easily washed away or rubbed from the surface. The compounds of the present invention are not only durable but retain their antimicrobial activity after some ten laundering cycles, and only slightly diminish in their activity after as many as twenty-five laundering cycles. The bound silanes of the present invention retain an effective kill level of microorganisms. The manner in which the bound silane functions differs from the unbound types, since the bound silane attaches itself to the surface to which it is applied, whereas the unbound types are mere coatings which are not substantive. This is significant since the silane antimicrobial will continue to prevent reinfestation, and enables one to utilize the intrinsic antimicrobial activity o the silane treated surface to kill transient microbes, long after the unbound types of antimicrobials have been depleted of their activity. Further, the bound silanes of the present invention destroy, reduce, and inhibit the growth and multiplication of bacteria, fungi, and other pathogenic microorganisms, by the disruption of cell membranes, a mechanism absent from conventional unbound antimicrobial materials. The results produced by the bound silanes is not the same as the results produced by the unbound types, since the bound silanes provide a prolonged antimicrobial activity and continue to kill and inhibit the proliferation of potentially destructive microorganisms, versus mere temporary and superficial protection offered by the unbound category of material. Thus, it should be apparent that the method of the present invention in employing the bound antimicrobially active organosilicon quaternary ammonium compounds is far removed from methods that have been previously disclosed by the prior art.

Bound antimicrobials kill organisms on contact and continue to kill organisms without being diffused or leached from the surface. Thus, the bound antimicrobial leaves behind an effective level of active ingredient and is able to control a broad spectrum of microorganisms including gram negative and gram positive bacteria, mold, mildew, fungi, yeast, and algae. An exemplary category of bound antimicrobial is an alkoxysilane quaternary ammonium compound, and such alkoxysilane quaternary ammonium compounds have been found to be more effective at reducing the number of microorganisms, and inhibiting microbially generated odors, than conventional organotin compounds and other organic quaternary ammonium compounds. The silanes of the present invention when delivered from simple water solutions immobilize on surfaces and bond thereto to provide a coating of immobilized antimicrobial, unlike conventional materials.

In the present invention, this bound characteristic of alkoxysilane quaternary ammonium compounds, as well as their capabilities of performing at effective kill levels beyond prior art types of compositions, is taken advantage of in the treatment of surfaces, in order to reduce or substantially eliminate the incidence of microorganisms, germs, their metabolic products and their somatic and reproductive cell parts, which contribute to the spread of such microbes.

It is not new to disinfect aqueous solutions in an attempt to rid the solutions of bacterial growth. For example, U.S. Pat. No. 1,204,171, issued Nov. 7, 1916, discloses a sanitary drinking tube which includes a body of disinfecting material. Water is said to be drawn through the disinfecting material and filtered or rendered free from contamination, although the exact nature and construction of the disinfecting material is not disclosed. In U.S. Pat. No. 4,483,771, issued Nov. 20, 1984, a liquid filter of multiple layers is taught, one layer of which is impregnated with an antibiotic bacteria destroying material such as penicillin, iodine, tetracycline, kanamycin, or sulfonamides. A dispenser for saline solution is taught in U.S. Pat. No. 4,463,880, issued Aug. 7, 1984. The saline dispenser includes a disinfectant soaked pad, although the composition of the disinfectant is not disclosed. In contrast, the present invention in one embodiment is directed specifically to opthalmic solutions and to the treatment of such solutions with a "bound" silane antimicrobial. Such a bound antimicrobial avoids the negative effects that traditional "unbound" antimicrobials possess. For example, it is known that many preservatives cause eye irritation to many people, and the foregoing unbound antimicrobials of the type noted immediately above in the '171, '771, and '880 patents would be no exception. In fact such unbound antimicrobials would in all likelihood possess irritation levels well in excess of the levels experienced with current preservative type compounds. This is particularly significant when it is considered that opthalmic solutions are traditionally administered in the form of drops directed to the area of the human eye. This highly sensitive area of the human anatomy is prone to irritation, and hence the presence of any leachable material in a filter medium used to treat such solutions which may tend to cause irritation to the eye should be avoided. Hence, the "bound" silane antimicrobial of the present invention offers significant advantages in that once the silane is chemically bonded to a surface such as a porous filter medium, the silane is substantive to that surface and is not carried away from the surface to the eye along with the filter effluent. In addition, the silane of the present invention maintains the ophthalmic solution in a sterile condition in the container, and causes any excess draining back into the container following administration to be re-sterilized. The addition of other preservatives for the ophthalmic solution is therefore eliminated.

The '171, '771, and '880 patents discussed above all suffer from the additional disadvantages in that the disinfectants and antibiotics disclosed therein are washable from the filter surfaces, and while some of the microorganisms may be killed to some extent, the solution sought to be preserved would actually become contaminated with the disinfectant or antibiotic. In leaching from the filter surfaces, the disinfectants would present the problem of raw toxicity to the eyes and skin, and a limited spectrum of activity. The antibiotics on the other hand, would create allergenic response sensitivities, a general chemical incompatability with the solution sought to be preserved, and the lack of a broad spectrum activity against a variety of microbial contaminates. Microorganisms also possess the capability of quickly adapting to most antibiotics.

SUMMARY OF THE INVENTION

This invention is directed to a method of dispensing an aqueous fluid which is desired to be maintained in a sterile condition by storing a quantity of aqueous fluid in a reservoir within a portable container having an outlet. The aqueous fluid is preferably an opthalmic fluid such as a saline solution which is free of preservatives. A porous filter medium is arranged within the container adjacent the outlet, and the aqueous ophthalmic preservative free saline solution is caused to pass from the reservoir through the porous medium and to the outlet. The porous filter medium has covalently bonded thereto an antimicrobially effective amount of an organosilicon quaternary ammonium compound, and the organosilicon quaternary ammonium compound is an organosilane having the formula selected from the group consisting of

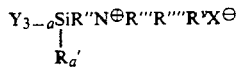

and

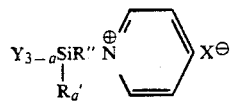

wherein, in each formula,

Y is R or RO where each R is an alkyl radical of 1 to 4 carbon atoms or hydrogen;

a has a value of 0, 1 or 2;

R' is a methyl or ethyl radical;

R" is an alkylene group of 1 to 4 carbon atoms;

R''', R'''' and $R^v$ are each independently selected from a group consisting of alkyl radicals of 1 to 18 carbon atoms, $-CH_2C_6H_5$, $-CH_2C_2OH$, $-CH_2OH$, and $-(CH_2)_xNHC(O)R^{vi}$, wherein x has a value of from 2 to 10 and $R^{vi}$ is a perfluoroalkyl radical having from 1 to 12 carbon atoms; and x is chloride, bromide, fluoride, iodide, acetate or tosylate.

The porous filter medium may be constructed of various materials, however, the filter is preferably constructed of a fiber strand such as of rayon, wool, nylon, cotton, silk, cellulose triacetate, polypropylene, polycarbonate, fiberglass, and polyester. The method is applicable to a wide variety of fluids in general, but is most convenient for the treatment of fluids such ophthalmic solutions, saline salt solutions, water delivered medicines, surgical irrigation fluids, water, milk, and emulsions. Often, the filter may not be sufficient for microbial decontamination, and therefore it has been found to be advantageous to bond the organosilane to the outer surfaces of the portable container as well as to the inner surfaces thereof. This internal and external container treatment is adapted for use in addition to the treatment of the porous filter with the organosilane. In severe cases, it may even become necessary to include an organosilane bound porous material in the bottom of the container reservoir for added microbial decontamination. This is most practically carried out with a porous material in the form of beads or fibers.

These and other features, objects, and advantages, of the present invention will be apparent when considered in light of the following detailed description thereof.

IN THE DRAWINGS

FIG. 1 is a pictorial representation shown in cross-section of a liquid dispensing device in accordance with the present invention.

FIG. 2 is a pictorial representation of the dev    illustrated in FIG. 1 and shown partially in cross-section. The device is oriented in a fashion to assimilate the position of the device when it is tilted with the hand of the user in order to apply drops of solution contained therein.

DETAILED DESCRIPTION OF THE INVENTION

Ammonium compounds in which all of the hydrogen atoms on nitrogen have been substituted by alkyl groups are called quaternary ammonium salts. These compounds may be represented in a general sense by the formula:

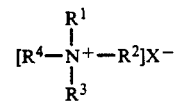

The nitrogen atom includes four covalently bonded substituents that provide a cationic charge. The R groups can be any organic substituent that provides for a carbon and nitrogen bond with similar and dissimilar R groups. The counterion X is typically halogen. Use of quaternary ammonium compounds is based on the hydrophilic portion of the molecule which bears a positive charge. Since most surfaces are negatively charged, solutions of these cationic surface active agents are readily adsorbed to the negatively charged surface. This affinity for negatively charged surfaces is exhibited by 3-(trimethoxysilyl)propyldimethyloctadecyl ammonium chloride hereinafter referred to as "TMS". This compound is manufactured by the Dow Corning Corporation, Midland, Mich., and has the formula:

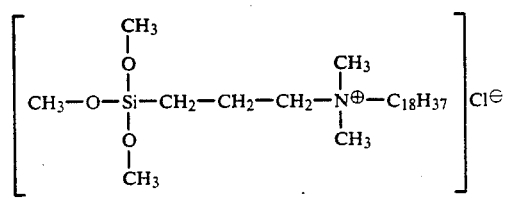

In the presence of moisture, this antimicrobial agent imparts a durable, wash resistant, broad spectrum biostatic surface antimicrobial finish to a substrate. The organosilicon quaternary ammonium compound is leach resistant, nonmigrating, and is not consumed by microorganisms. It is effective against gram positive and gram negative bacteria, fungi algae, yeasts, mold, rot, and mildew. The quaternary ammonium complex provides durable, bacteriostatic, fungistatic, and algistatic surfaces. It can be applied to organic or inorganic surfaces as a dilute aqueous or solvent solution of 0.1-1.5 percent by weight of active ingredient. After the alkoxysilane is applied to a surface, it is chemically bonded to the substrate by condensation of the silanol groups at the surface. The pure compound is crystalline whereas methanol solutions of the compound are low viscosity, light to dark amber liquids, soluble in water, alcohols, ketones, esters, hydrocarbons, and chlorinated hydrocarbons. The compound has been used in applications such as, for example, socks, filtration media, bed sheets, blankets, bedspreads, carpet, draperies, fire hose fabric materials, humidifier belts, mattress pads, health care apparel, mattress ticking, underwear, nonwoven disposable diapers, nonwoven fabrics, outerwear fabrics, nylon hosiery, vinyl paper, wallpaper, polyurethane cushions, roofing materials, sand bags, tents, tarpaulins, sails, rope, blood pressure cuffs, athletic and casual shoes, shoe insoles, shower curtains, toilet tanks, toilet seat covers, throw rugs, towels, umbrellas, upholstery fiberfill, intimate apparel, wiping cloths, and medical devices such as blood pressure cuffs.

The silanes useful in this invention have the general formula

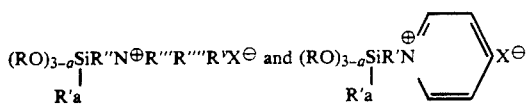

It should be noted that generically, these materials are quaternary ammonium salts of silanes. Most of the silanes falling within the scope of this invention are known silanes and references disclosing such silanes are numerous. One such reference, U.S. Pat. No. 4,259,103, issued to James R. Malek and John L. Speier, on Mar. 31, 1981, discusses the use of such silanes to render the surfaces of certain substrates antimicrobial. British Patent No. 1,433,303, issued to Charles A. Roth shows the use of fillers treated with certain silanes to be used in paints and the like to give antimicrobial effects. Numerous publications have disclosed such silanes, for example, A. J. Isquith, E. A. Abbott and P. A. Walters, *Applied Microbiology*, Vol. 24, No. 6, Dec., 1972, pages 859-863.

For purposes of this invention, the silanes can be used neat or they can be used in solvent or aqueous-solvent solutions. When the silanes are used neat, the inventive process is preferably carried out in a system in which some small amount of water is present. If it is not possible to have a system with some small amount of water present, then a water soluble or water-dispersable, low molecular weight hydrolyzate of the silane may be used. What is important is the fact that the durability of any effect produced by the silane as part of a product requires that the silane molecule react with a surface to a certain extent. The most reactive species, as far as the silanes are concerned, is the ≡SiOH that is formed by hydrolysis of the alkoxy groups present on the silane. The ≡SiOH groups tend to react with the surface and bind the silanes to the surface. It is believed by the inventor that even though the prime mode of coupling to the surface system is by the route described above, it is also believed by the inventor that the alkoxy groups on the silicon atom may also participate in their own right to bind to the surface.

Preferred for this invention is a reactive surface containing some small amount of water. By "reactive", it is meant that the surface must contain some groups which will react with some of the silanols generated by hydrolysis of the silanes of this invention.

R in the silanes of this invention are alkyl groups of 1 to 4 carbon atoms. Thus, useful as R in this invention are the methyl, ethyl, propyl and butyl radicals. In the above formulas RO can also be R. R can also be hydrogen thus indicating the silanol form, i.e. the hydrolyzate. The value of a is 0, 1 or 2 and R' is a methyl or ethyl radical. Because of the presence of these alkyl radicals, the prior art teaches that the materials must be stabilized with a corresponding solvent. Thus, methoxy groups require methanol and ethoxy groups require ethanol, for example.

R" for purposes of this invention is an alkylene group of 1 to 4 carbon atoms. Thus, R" can be alkylene groups such as methylene, ethylene, propylene, and butylene. R''', R'''', and R$^v$ are each independently selected from a group which consists of alkyl radicals of 1 to 18 carbons, —CH$_2$C$_6$H$_5$, —CH$_2$CH$_2$OH, —CH$_2$OH, and —(CH$_2$)$_x$NHC(O)R$^{vi}$. x has a value of from 2 to 10 and R$^{vi}$ is a perfluoroalkyl radical having from 1 to 12 carbon atoms. X is chloride, bromide, fluoride, iodide, acetate or tosylate.

Preferred for this invention are the silanes of the general formula

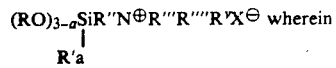

R is methyl or ethyl; a has a value of zero; R" is propylene; R''' is methyl or ethyl; R'''' and R$^v$ are selected from alkyl groups containing 1 to 18 carbon atoms wherein at least one such group is larger than eight carbon atoms and x is either chloride, acetate or tosylate.

Specific silanes within the scope of the invention are represented by the formulae:

(CH$_3$O)$_3$Si(CH$_2$)$_3$N$^+$(CH$_3$)$_2$C$_{18}$H$_{37}$Cl$^-$,
(CH$_3$O)$_3$Si(CH$_2$)$_3$N$^+$(CH$_3$)$_2$C$_{18}$H$_{37}$Br$^-$,
(CH$_3$O)$_3$Si(CH$_2$)$_3$N$^+$(C$_{10}$H$_{21}$)$_2$CH$_3$Cl$^-$,
(CH$_3$O)$_3$Si(CH$_2$)$_3$N$^+$(C$_{10}$H$_{21}$)$_2$CH$_3$Br$^-$,
(CH$_3$O)$_3$Si(CH$_2$)$_3$N$^+$(CH$_3$)$_3$Cl$^-$,
(CH$_3$O)$_3$SiCH$_2$CH$_2$CH$_2$P$^+$(C$_6$H$_5$)$_3$Cl$^-$,
(CH$_3$O)$_3$SiCH$_2$CH$_2$CH$_2$P$^+$(C$_6$H$_5$)$_3$Br$^-$,
(CH$_3$O)$_3$SiCH$_2$CH$_2$CH$_2$P$^+$(CH$_3$)$_3$Cl$^-$,
(CH$_3$O)$_3$SiCH$_2$CH$_2$CH$_2$P$^+$(C$_6$H$_{13}$)$_3$Cl$^-$,
(CH$_3$)$_3$Si(CH$_2$)$_3$N$^+$(CH$_3$)$_2$C$_{12}$H$_{25}$Cl$^-$,
(CH$_3$)$_3$Si(CH$_2$)$_3$N$^+$(C$_{10}$H$_{21}$)$_2$CH$_3$Cl$^-$,
(CH$_3$)$_3$Si(CH$_2$)$_3$N$^+$(CH$_3$)$_2$C$_{18}$H$_{37}$ Cl$^-$,
(CH$_3$O)$_3$Si(CH$_2$)$_3$N$^+$(CH$_3$)$_2$C$_4$H$_9$Cl$^-$,
(C$_2$H$_5$O)$_3$Si(CH$_2$)$_3$N$^+$(CH$_3$)$_2$C$_{18}$H$_{37}$Cl$^-$,
(CH$_3$O)$_3$Si(CH$_2$)$_3$N$^+$(CH$_3$)$_2$CH$_2$C$_6$H$_5$Cl$^-$,
(CH$_3$O)$_3$Si(CH$_2$)$_3$N$^+$(CH$_3$)$_2$CH$_2$CH$_2$OHCl$^-$,

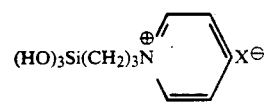

-continued

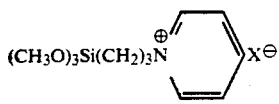

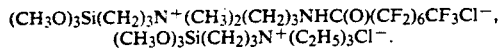

The treatment can be applied to the porous filter medium in the form of an emulsion including water, the silane, and a water immiscible liquid. The water immiscible liquid, or volatile as used in the emulsion, is a silicone oil which is highly volatile, and low in viscosity and molecular weight. For example, there may be employed trimethylsiloxy endblocked polydimethylsiloxanes, cyclic siloxanes such as dimethylsiloxane cyclic tetramer, and phenylmethyl fluids such as linear polyphenylmethylsiloxanes. Preferred for this invention are those silicone oils having a viscosity at twenty-five degrees Centigrade ranging from about 0.65 cs to about one thousand cs. A particularly preferred range is from about 0.65 cs to about 20 cs, although those silicone oils of viscosities of 50 cs, and 350 cs, can be employed. These silicone oils are more particularly described and set forth in detail in U.S. Pat. No. 4,631,273, issued Dec. 23, 1986, the disclosure of which is incorporated herein by reference. Such silicone oils are siloxanes which are low molecular weight cyclics and polysiloxanes having the general formula

wherein R' is an alkyl radical of 1 to 3 carbon atoms, phenyl, an alkoxy radical having the formula R''''O-, wherein R'''' is an alkyl radical of 1 to 4 carbon atoms or hydrogen; R'' is an alkyl radical of 1 or 2 carbon atoms or the phenyl group; R''' has the same meaning as R''; Q is a substituted or unsubstituted radical composed of carbon and hydrogen, or carbon, hydrogen and oxygen, or carbon, hydrogen and sulfur, or carbon, hydrogen and nitrogen; w has a value of from 1 to 500; z has a value of 1 to 25 and y has a value of 3 to 8.

The organosilane may also be employed in accordance with the present invention in the form of a microemulsion containing the organosilane. Such microemulsions and their preparation are described in U.S. Pat. No. 4,842,766, issued June 27, 1989. Solutions with particle sizes less than 0.150 microns are disclosed which are either oil-in-water or water-in-oil microemulsions including the organosilane and at least one surfactant. The '766 patent relating to the microemulsions is considered incorporated herein by reference.

Various procedures are employed in order to test the organosilanes of the present invention. For example, the presence of the chemical on a substrate can be determined by complexing a standardized solution of bromophenol blue in water with the quaternary nitrogen of the organosilane and recording the color change spectrophotometrically. Results of this test can be used in order to determine whether the organosilane has bound itself to a particular surface. Such a test procedure is set forth below.

The anion of an aqueous sodium salt of bromphenol blue can be complexed with the cation of polymerized silanes of this invention while on a substrate. The blue colored complex, substantive to a water rinse, is qualitatively indicative of the presence of the cation on the substrate thus indicating the extent of antimicrobial agent on a given substrate. A comparison of the intensity of retained blue color to a color standard is used as a check to determine if the treatment has been applied properly.

One method consists of preparing a 0.02 to 0.04 weight percent solution of bromphenol blue in distilled water. This solution is made alkaline using a few drops of saturated $Na_2CO_3$ solution per 100 milliliters of the solution. Two to three drops of this solution are placed on the treated substrate and allowed to stand for two minutes. The substrate is then rinsed with copious amounts of tap water and the substrate is observed for a blue stain and it is compared to a color standard.

For a spectrophotometric determination, the following test is used. The sodium salt of bromphenol blue is depleted from a standard solution by complexing with the cations on a treated substrate. The change in bromphenol blue concentration is determined spectrophotometrically or by comparison with color standards whereby the level of substrate treatment by the cationic silane is determinable.

The method consists of preparing a 0.02 weight percent standard solution of bromphenol blue in distilled water. It is made alkaline with a few drops of saturated $Na_2CO_3$ solution per 100 milliliters of bromphenol blue solution. The color of this solution is purple. The blank solution is adjusted to yield a 10 to 12% transmittance reading when measured in 1 cm cells using a spectrophotometer set at 589 nm by the following method. Fill a container ¾ full of distilled water and add 2 ml of the 0.02% standard bromphenol blue solution for every 50 ml of distilled water. Add 0.5 ml of a 1% Triton ® X-100 surfactant (manufactured by Rohm and Haas, Philadelphia, Pa., USA) aqueous solution for every 50 ml of water. Mix, and using the spectrophotometer, determine the maximum absorbance. Adjust the upper zero to 100% transmittance with distilled water. Check the percent transmittance of the working bromphenol blue solution at the maximum absorbance setting. Adjust the blank solution to 10 to 12% transmittance with either water or bromphenol blue standard solution as necessary.

The samples of treated substrate can be tested by placing 0.5 gram samples of the substrate standard in a flask large enough for substantial agitation of the sample and the test solution. Add 50 ml of the working solution. Agitate for 20 minutes on a wrist-action shaker. Fill the test curvette with the test solution. Centrifuge if particulate matter is present. Measure the % transmittance at the wavelength set forth above. The transmittance is compared against a standard curve prepared by preparing several substrate samples of known concentration of the cationic silane. For example, samples containing a known amount of cationic silane at, for example, 0%, 0.25%, 0.50%, 0.75% and 1% are read spectrophotometrically and a curve is plotted.

The antimicrobial activity of a treated surface is normally evaluated by shaking a sample weighing 0.75 grams in a 750,000 to 1,500,000 count *Klebsiella pneumoniae* suspension for a one hour contact time. The suspension is serially diluted, both before and after contact, and cultured. The number of viable organisms in the suspensions is determined. The percent reduction based on the original count is determined. The method is intended for those surfaces having a reduction capability of 75 to 100% for the specified contact time. The results are reported as the percent reduction. Media used in this test are nutrient broth, catalog No. 0003-01-6 and tryptone glucose extract agar, catalog No. 0002-01-7 both available from Difco Laboratories, Detroit, Mich., U.S.A. The microorganism used is *Klebsiella pneumoniae* American Type Culture Collection; Rockville, Md. U.S.A., catalog No. 4352. The procedure used for determining the zero contact time counts is carried out by utilizing two sterile 250 ml. screw-cap Erlenmeyer flasks for each sample. To each flask is added 70 ml of sterile buffer solution. To each flask is added, aseptically, 5 ml of the organism inoculum. The flasks are capped and placed on a wrist action shaker. They are shaken at maximum speed for 1 minute. Each flask is considered to be at zero contact time and is immediately subsampled by transferring 1 ml of each solution to a separate test tube containing 9 ml of sterile buffer. The tubes are agitated with a vortex mixer and then 1 ml of each solution is transferred to a second tube containing 9 ml of sterile buffer. Then, after agitation of the tubes, 1 ml of each tube is transferred to a separate sterile petri dish. Duplicates are also prepared. Sixteen ml of molten (42° C.) tryptone glucose extract agar is added to each dish. The dishes are each rotated ten times clockwise and ten times counterclockwise. The dishes are then incubated at 37° C. for 24 to 36 hours. The colonies are counted considering only those between 30 and 300 count as significant. Duplicate samples are averaged. The procedure used for determining the bacterial count after 1 hour is essentially the same as that used to determine the count at the zero contact time. The only difference is that pour plating is performed at the $10^0$ and $10^{-1}$ dilutions as well as at the $10^{-2}$ dilution. "Percent reduction" is calculated by the formula $$\% R = \frac{\frac{B + C}{2} - A_{100}}{\frac{B + C}{2}}$$

where A is the count per milliliter for the flask containing the treated substrate; B is zero contact time count per milliliter for the flask used to determine "A" before the addition of the treated substrate and C is zero contact time count per milliliter for the untreated control substrate.

The foregoing "Shake Flask Test" measures antimicrobial substrate activity. An alternative test sometimes employed is the "Agar Plate Graphing Technique" which again affords a measure of antimicrobial substrate activity, in which treated swatches of fabric are placed on agar impregnated with *Klebsiella pneumoniae*. Antimicrobial activity is measured by the existence of a zone of inhibition and diffusability in the agar. Immobilized antimicrobials will not show a zone.

It is also possible to measure antimicrobial solution activity and this is performed in accordance with the procedures of the "Minimum Inhibitory Concentration Test" (MIC) in which the level of chemical required to inhibit the growth of microorganisms in a system is determined, typically employing organisms such as *Staphylococcus aureus, Klebsiella pneumoniae*, and *Aspergillus niger*.

One species of organosilane and the preferred organosilicon quaternary ammonium compound in accordance with the present invention is 3-(trimethoxysilyl) propyldimethyloctadecyl ammonium chloride of the formula:

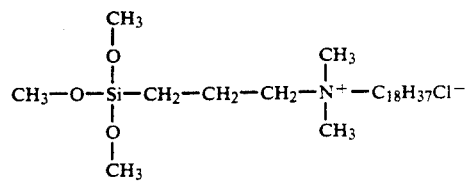

This complex molecule has three active areas. The presence in the molecule of the long chain aliphatic alkyl group $C_{18}H_{37}$ which is non-polar and oil-like, determines the hydrophobic/oleophilic properties of the molecule. The molecule attaches itself to surfaces via the methoxy silane functionality which serves as the anchor or coupler, whereas the quaternary ammonium salt functionality portion of the molecule which is cationically charged, performs the antimicrobial or microorganism killing function. It is this unique and complex arrangement which sets the organosilicon compounds of the present invention apart from the conventional organic antimicrobial materials of the prior art.

Regarding the activity of the compounds of the present invention, such compounds have been found to be effective against a number of microorganisms, such as "BACTERIA": Gram (−); *Escherichia coli, Klebsiella pneumoniae, Klebsiella oxytoca, Pseudomonas aeruginosa, Pseudomonas fluorescens, Proteus mirabilis, Proteus vulgaris, Salmonella typhi, Salmonella typhimurium, Salmonella cholera suis, Enterobacter cloacae, Enterbacter aerogenes, Morganella morganii, Aeromonas hydrophila, Citrobacter freundii, Citrobacter deversus, Serratia marcescens, Serratia liquifaciens, Xanthomonas campestris, Acinetobacter calcoaceticus*; Gram (+): *Staphylococcus aureus, Staphylococcus epidermidis, Streptococcus mutans, Streptococcus pyogenes, Streptococcus fecalis, Micrococcus lutea, Bacillus* sp. (vegetative cell); "Fungi": *Aspergillus niger, Aspergillus flavus, Aspergillus sydowi, Aspergillus versicolor, Aspergillus terreus, Penicillium chrysogenum, Penicillium variabile, Penicillium funiculosum, Penicillium pinophilum, Poria placenta, Aureobasidium pullulans, Gloeophyllum trabeum, Chaetomium gobosum, Trichoderma viride, Trichophyton mentagrophytes*; "Fungi" (yeasts): *Candida albicans, Candida pseudotropicalis, Saccharomyces cerevisiae*.

The treatment disclosed herein can be carried out with the quaternary ammonium compounds of this invention per se. Often, however, it is desirable to extend the compounds of this invention by incorporating therein hydrocarbon or halohydrocarbon substituted siloxanes of the formula

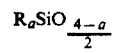

in which R is a hydrocarbon or halohydrocarbon radical and a varies from 0 to 3. The incorporation of such siloxanes in no way effects the property of the quaternary ammonium compound so that the claims of this invention are construed to cover both the use of quaternary ammonium siloxane per se and mixtures or copolymers of such siloxanes with said hydrocarbon substitutes siloxanes or halohydrocarbon substituted siloxanes. For example, surfaces can be treated with an aqueous solution of a mixture of 10 mols of monomethyl trimethysilane and 1 mol of $Cl^-C_{18}H_{37}Me_2N^+(CH_2)_3Si(OMe)_3$. It has also been found that combinations of 1 mol Cl$^-$C$_{18}$H$_{37}$Me$_2$N$^+$(CH$_2$)$_3$Si(OMe)$_3$ and 0.5 mol of 3-chloropropyltrimethoxysilane give effective siloxane coatings. The use of hydrocarbon and halohydrocarbon siloxane extenders often give cheaper, more durable, more oleophilic or oleophobic surface treatments, than the pure quaternary siloxane.

The process of the present invention can be best described with reference to the accompanying drawing in which the container for dispensing an ophthalmic solution is shown generally at 10 in FIGS. 1 and 2. The liquid dispenser 10 will be seen to include a flexible wall 11 which forms a reservoir for storing saline solution 12. In accordance with the present invention, the solution is preferably free of preservative. Container 10 has an upper section 13 which includes exterior threads, and the exterior threads mate with the interior threads 14 of the container cap 15. Cap 15 can also be integrally constructed with container wall 11, if desired. Cap 15 encloses and forms a chamber 18 which houses a porous filter medium. The filter medium is retained in the chamber 18 by a screen mesh support 17 which is positioned and held within the cap 15 by an interior lip 20. An outlet 19 extends axially of cap 15 and provides communication between the reservoir 12 of saline fluid and the exterior of the container 10. As the container is tilted by the hand 22 of the user in the direction of arrows 16, as shown in FIG. 2, drops 21 of saline solution are directed to the area of the eye of the user. When the container is returned to its upright position as shown in FIG. 1, excess saline solution in outlet 19 drains back into reservoir 12 through the porous filter medium 18. The device also includes a cover for the outlet which is not shown in the drawings.

Treatment of the porous filter medium 18 with the organosilicon quaternary ammonium compounds of the present invention results in a covalent bond which chemically unites the organosilicon antimicrobial compound to the surfaces of the porous filter medium. This provides that the bound antimicrobial will not leach into the reservoir or pass into the eye with the drops 21, as do conventional unbound type antimicrobials and disinfectants. This is particularly significant in the present instance in that the various opthalmic solutions intended herein are delivered to the highly sensitive area of the human eye.

The wall 11 of the portable container 10 is constructed of a flexible material in order that the container wall may be squeezed to force the contents of the container from the reservoir 12 through the porous filter medium 18 and into the outlet 19. The flexible material is preferably one of polyethylene, polypropylene, and acrylic polymers. The porous filter medium 18 may be one of a variety of materials suitable for liquid filtration among which are those filter materials constructed of a fiber strand such as rayon, wool, nylon, cotton, silk, cellulose triacetate, polypropylene, polycarbonate, fiberglass, and polyester. The porous filter medium can also be of a cellular structure of a foam material such as polyurethane, polystyrene, polyvinyl chloride, polyethylene, and polypropylene. In addition, the porous filter medium may be a high surface area particulate material such as silica, ceramic, sintered metal, and sintered glass. Other materials which can be used for the porous filter medium are paper, mesh screen, and glass beads. Glass containers can also be used but the flexible construction is the preferred embodiment.

In addition to treatment of the porous filter medium 18 with the organosilane, and in order to further eliminate the problem of microbial contamination and buildup of microorganisms, both the inner and outer surfaces of the container 10 should be treated with the organosilane in order to bind the organosilane to these surfaces. This treatment should include especially the area surrounding the outlet 19, particularly the cap 15, as well as the container walls 11. In the case of ophthalmic applications of the present invention, such treatment avoids the contamination caused by touching the cap to the eye area upon administration of the contents of the container to the eye. Such surface coverage of the container interior and exterior walls is set forth in Example I. Treatment may be further enhanced by adding directly to the contents of the reservoir 12 a loose organosilane bound porous material. This concept is shown in Example III. Wetting agents such as fluorocarbon, nonionic, and cationic surfactants, may also be combined with the organosilane in the treatment process, and this embodiment is set forth in Example II. Example IV is directed to the concept of employing the organosilane in the most effective amount which is shown to be at least in excess of about 0.5 percent by weight of the organosilane based on the total weight of the surface being treated, and preferably in an amount of about 0.75 percent by weight.

EXAMPLE I

Containers of polyethylene, polypropylene and glass were treated by exhaustion while immersed in 140 degree Fahrenheit tap water, 1% by weight solution of a 42% active 3-(trimethoxysilyl)propyldimethyloctadecyl ammonium chloride for four hours. Samples were dried in a forced air oven at 90 degrees Centigrade for two hours. Glass beads, cigarette filters of cellulose triacetate, #1 Whatman filter paper, and styrene maleic anhydride (SMA) beads were treated as above. Bromophenol blue tests for intensity of color and uniformity of treatment were performed by immersion to treated and control substrates for five minutes immersion and at ambient room temperature. The #1 Whatman filter paper and the cigarette filters were tested by a padding test, the beads and plastic containers were tested by the dynamic shake flask test.

In the padding test, the bacteriostatic activity of fabric or an antibacterial agent applied to a standard fabric is evaluated. Test and control fabric swatches are inoculated with the test organism. Immediately after inoculation and after six hours of contact time, the bacteria are eluted from selected swatches by shaking in a known amount of solution. The number of bacteria present in the two solutions is determined. The percent reduction after the six hour contact is calculated and reported. This method is based on AATCC Test Method 100.

The results of the tests of Example I are shown in Table I.

TABLE I

| Sample | | Analytical (BPA) | | % Reduction[2] | |
|---|---|---|---|---|---|
| | | Intensity[1] | Uniformity | Padding | Shake Flask |
| PE Bottle | Treated | 2 | complete | NR[6] | 100[5] |
| | Control | 4 | None | NR | 0[5] |
| PP Bottle | Treated | 3 | Complete | NR | 100[5] |
| | Control | 4 | None | NR | 0[5] |
| Glass Bottle | Treated | 2 | complete | NR | NR |
| | Control | 4 | None | NR | NR |
| Glass Beads | Treated | 2 | complete | NR | 100 |
| | Control | 4 | None | NR | 0 |
| SMA Beads | Treated | 2 | Complete | NR | 100 |
| | Control | 4 | None | NR | 0 |

TABLE I-continued

| Sample | | Analytical (BPA) | | % Reduction[2] | |
|---|---|---|---|---|---|
| | | Intensity[1] | Uniformity | Padding | Shake Flask |
| Whatman #1 | Treated | 1 | Complete | 100[3] | NR |
| | Control | 4 | None | 0 | NR |
| CTA Filter | Treated | 1 | Complete | 100[4] | 100 |
| | Control | 4 | None | 0 | 0 |

[1]Intensity: 1 - Dark Purple, 2 - Medium Purple, 3 - Light Purple, 4 - No Retention.
[2]Klebsiella Pneumoniae, one hour.
[3]Eight Circles.
[4]Teased apart and placed in bottom of tube for padding.
[5]Two grams cut in small pieces.
[6]NR - not run.
PE = Polyethylene
PP = Polypropylene
CTA = Cellulose Triacetate The test protocol above provides data from which it can be concluded that all of the test substrates were uniformly treated with the test compounds and that surfaces were antimicrobial.

EXAMPLE II

To minimize treatment time and to optimize uniformity, a test using a wetting agent was conducted. Substrates as in Example I were treated by exhaustion by immersion in ambient room temperature tap water with a 1% by weight solution of a 42% 3-(trimethoxysilyl)-propyldimethyoctadecyl ammonium chloride for 1 minute, 5 minute, 10 minute and 20 minute intervals. Samples were dried in a forced air oven at 90 degrees Centigrade for two hours. The treatment bath contained 0.05% by weight of a fluorocarbon surfactant Zonyl ® FSN. The surfactant can be any nonionic or cationic wetting agent.

Bromophenol blue tests were performed and the results of these tests are shown below in Table II.

TABLE II

| | | BPA Analytical Ratings/Treatment Immersion Times | | | | | | | |
|---|---|---|---|---|---|---|---|---|---|
| | | 1 Minute | | 5 Minutes | | 10 Minutes | | 20 Minutes | |
| Sample | | Intensity[1] | Uniformity | Intensity | Uniformity | Intensity | Uniformity | Intensity | Uniformity |
| PE Bottle | Treated | 4 | None | 3 | Pools | 3 | Complete | 2 | Complete |
| | Control | 4 | None | 4 | None | 4 | None | 4 | None |
| PP Bottle | Treated | 4 | None | 3 | Pools | 3 | Complete | 2 | Complete |
| | Control | 4 | None | 4 | None | 4 | None | 4 | None |
| Glass Bottle | Treated | 3 | Pools | 2 | complete | 2 | complete | 2 | Complete |
| | Control | 4 | None | 4 | None | 4 | None | 4 | None |
| Glass Beads | Treated | 3 | Pools | 3 | Pools | 3 | Complete | 2 | Complete |
| | Control | 4 | None | 4 | None | 4 | None | 4 | None |
| SMA Beads | Treated | 4 | None | 3 | Pools | 2 | Complete | 2 | Complete |
| | Control | 4 | None | 4 | None | 4 | None | 4 | None |
| Whatman #1 | Treated | 2 | Complete | 1 | Complete | 1 | Complete | 1 | Complete |
| | Control | 4 | None | 4 | None | 4 | None | 4 | None |
| CTA Filter | Treated | 2 | Complete | 1 | Complete | 1 | Complete | 1 | Complete |
| | Control | 4 | None | 4 | None | 4 | None | 4 | None |

[1]Intensity: 1 - Dark Purple, 2 - Medium Purple, 3 - Light Purple, 4 - No Retention.

The test protocol of Example II and Table II provides data from which it can be concluded that the wetting agent enhances room temperature exhaustion such that all substrates were uniformly treated within 10 minutes.

The Whatman #1, and CTA filters were uniformly treated in one minute, the SMA and glass beads and the PE and PP bottles in 10 minutes, and the glass bottle in 5 minutes.

EXAMPLE III

Contaminated Solution Test Using Various Bottle/Substrate-Filter/Substrate Configurations All test substrates were treated as in Example I. A phosphate buffer solution of a 24 hour culture of *Klebsiella pneumoniae* at $1.4 \times 10^5$/ml was prepared. Twenty milliliters of this inoculum was placed into test container configurations and agitated on a rotary shaker for one hour. Plate counts were performed using standard plate count procedures. The results of these tests are shown in Table III.

TABLE III

| Sample | | Microbial Plate Counts % Reduction |
|---|---|---|
| PE Bottle 2 oz. | Treated | 99.99 |
| | Control | 0 |
| PP Bottle 2 oz. | Treated | 99.98 |
| | Control | 0 |
| Glass Bottle 2 oz. | Treated | 99.98 |
| | Control | 0 |
| PE Bottle 2 oz. 0.5 g Glass Beads* | Treated | 100 |
| | Control | 0 |
| PP Bottle 2 oz. 0.5 g Glass Beads* | Treated | 100 |
| | Control | 0 |
| Glass Bottle 2 oz. 0.5 g Glass Beads* | Treated | 100 |
| | Control | 0 |
| PE Bottle 2 oz. 0.5 g CTA Filter* | Treated | 100 |
| | Control | 0 |
| PP Bottle 2 oz. 0.5 g CTA Filter* | Treated | 100 |
| | Control | 0 |
| Glass Bottle 2 oz. 0.5 g CTA Filter* | Treated | 100 |
| | Control | 0 |

* = Material including organosilane placed in container.

The test protocol of Example III and Table III provides data from which it can be concluded that the control bottles and filter configurations did not affect microbial growth; that sanitizing levels of reduction were reached with all treated samples; and that the use of the treated glass beads or CTA filter inserts significantly improved the microbial kill.

EXAMPLE IV

The substrate for filtering materials was Filterol ®, CTA cigarette filter. This test was conducted to determine an optimal treatment level. The Filterol ® CTA filters were treated as in Example I except that a concentration series of 0.25%, 0.5%, 0.75% and 1% of 42% active 3-(rimethoxysilyl)propyldimethyloctadecyl ammonium chloride by weight of the substrate was employed in the exhaustion procedure. A 20 minute exhaustion period was employed. Analytical checks of the post exhaustion bath showed no detectable active ingredient. All samples were tested with bromophenol blue, and the Shake Flask Test was performed as outlined above. Results of these tests are set forth in Table IV.

TABLE IV

| Sample | | Analytical % Transmission | Microbiological % Reduction |
|---|---|---|---|
| Filterol ® | Control | 12.0 | 12.8 |
| Filterol ® | 0.25% TMS | 14.0 | 15.7 |
| Filterol ® | 0.50% TMS | 14.0 | 40.5 |
| Filterol ® | 0.75% TMS | 15.0 | 99.6 |
| Filterol ® | 1.00% TMS | 16.0 | 99.6 |

Table IV indicates that the preferred level of treatment with the organosilane TMS to provide desired efficacy as an antimicrobial filter medium is in excess of at least about 0.50% by weight of the organosilane, preferably about 0.75%.

EXAMPLE V

Simulated In Use Test—Antimicrobial Package System

A total package system was constructed to provide optimal construction for mitigating microbial contamination of the fluid in the container from fill to empty-in-use. To accomplish this, a system of contamination, as if the tip of the bottle touched the eye (receiving contamination), was devised. The test system components were treated by exhaustion at 1% by weight of a 42% solution of 3-trimethoxysilylpropyldimethyl octadecyl ammonium chloride at 100° F. for 5 minutes with 0.1% Zonyl ® FSN wetting agent. Samples were dried at 90° C. in a forced air oven and put through a rinse cycle.

Each of the test bottles were aseptically assembled with the CTA filter 18 inserted into the neck of the delivery nipple and inserted into the neck of the bottle. Controls and treated samples were all treated identically. Various filter substrates such as urethane foam, cotton fabric, and paper, were treated as above, and inserted as needed for testing.

To assure durability of the treatment, a deionized water rinse cycle test was undertaken with the treated substrates. Four hundred milliliters of deionized water were placed in a rinsed one pint French square bottle. The treated test system and untreated control were placed into a series of these bottles and shaken on a reciprocal shaker at ambient room temperature (21° C.) for 0 minutes, 1 minute, 5 minutes, 10 minutes and 20 minutes. Water samples were analyzed for 3-trimethoxysilylproplydimethyl octadecyl ammonium chloride using the quaternary ammonium sensitive bromophenol blue colorimetric test. Each of the samples were subjected to 3x of the above protocol. Samples were dried between cycles. It was found that 2x of the 5 minute rinse ridded the system of unreacted material and all microbiological tests were run with that system.

*Staphylococcus aureas, Escherichia coli* and *Pseudomonas aeruginosa* were cultured per the Preservative Challenge Test Requirements in the U.S. Pharmacopia. Cultures were standardized so that one drop contained between $10^5$ and $10^6$ organisms. A 0.1% tryptic soy broth (Difco) was prepared and sterilized. Five milliliters of broth was placed aseptically into 9 milliliters polyethylene dropper bottles. Tips and filter assemblies were inserted and tops arranged under aseptic conditions. A drop of the inoculum was aspirated into the test bottles. Separate bottles were checked for microbial presence at 24 hours, 14 days, and 28 days. Standard retrieval and counting techniques were used for the fluid. One milliliter was removed for serial dilution. The tips and filters were aseptically removed, placed in tubes of tryptic soy broth, incubated for 24 and 48 hours, and checked for growth turbidity, and recorded as (+) or (−). Identifications of the organisms were made. All tests were run in triplicate. The results are shown in Table V.

TABLE V

MICROBIOLOGICAL TEST
SIMULATED IN-USE TEST - ANTIMICROBIAL PACKAGE SYSTEM

| Organism | Run | TR | UNTR | Fluid Tests/CFU/ml | | | | Tip | | Filter | |
|---|---|---|---|---|---|---|---|---|---|---|---|
| | | | | 0 hr. | 24 hr. | 14 Days | 28 Days | 24 hr. | 48 hr. | 24 hr. | 48 hr. |
| *Staphloccoccus aureus* | 1 | X | | $2.6 \times 10^{4^1}$ | 0 | 0 | 0 | — | — | — | — |
| | 2 | X | | $2.6 \times 10^{4^1}$ | 0 | 0 | 0 | — | — | — | — |
| | 3 | X | | $2.6 \times 10^{4^1}$ | 0 | 0 | 0 | — | — | — | — |
| | 1 | | X | $2.6 \times 10^{4^1}$ | $>3 \times 10^7$ | $>3 \times 10^7$ | $>3 \times 10^7$ | ++ | +++ | +++ | +++ |
| | 2 | | X | $2.6 \times 10^{4^1}$ | $>3 \times 10^7$ | $>3 \times 10^7$ | $>3 \times 10^7$ | + | +++ | +++ | +++ |
| | 3 | | X | $2.6 \times 10^{4^1}$ | $>3 \times 10^7$ | $>3 \times 10^7$ | $>3 \times 10^7$ | + | +++ | +++ | +++ |
| *Escherichia coli* | 1 | X | | $3.56 \times 10^{4^2}$ | $3.1 \times 10^2$ | 0 | 0 | — | — | — | — |
| | 2 | X | | $3.56 \times 10^{4^2}$ | $2.6 \times 10^2$ | 0 | 0 | — | — | — | — |
| | 3 | X | | $3.56 \times 10^{4^2}$ | $2.7 \times 10^2$ | 0 | 0 | — | — | — | — |
| | 1 | | X | $3.56 \times 10^{4^2}$ | $>3 \times 10^7$ | $>3 \times 10^7$ | $>3 \times 10^7$ | + | +++ | +++ | +++ |
| | 2 | | X | $3.56 \times 10^{4^2}$ | $>3 \times 10^7$ | $>3 \times 10^7$ | $>3 \times 10^7$ | ++ | +++ | +++ | +++ |
| | 3 | | X | $3.56 \times 10^{4^2}$ | $>3 \times 10^7$ | $>3 \times 10^7$ | $>3 \times 10^7$ | + | +++ | +++ | +++ |
| *Pseudomona aeuroginosa* | 1 | X | | $3.84 \times 10^{4^3}$ | $3.1 \times 10^1$ | 0 | 0 | — | — | — | — |
| | 2 | X | | $3.84 \times 10^{4^3}$ | $6.8 \times 10^1$ | 0 | 0 | — | — | — | — |
| | 3 | X | | $3.84 \times 10^{4^3}$ | $4.3 \times 10^1$ | 0 | 0 | — | — | — | — |
| | 1 | | X | $3.84 \times 10^{4^3}$ | $>3 \times 10^7$ | $>3 \times 10^7$ | $>3 \times 10^7$ | ++ | +++ | +++ | +++ |
| | 2 | | X | $3.84 \times 10^{4^3}$ | $>3 \times 10^7$ | $>3 \times 10^7$ | $>3 \times 10^7$ | + | +++ | +++ | +++ |
| | 3 | | X | $3.84 \times 10^{4^3}$ | $>3 \times 10^7$ | $>3 \times 10^7$ | $>3 \times 10^7$ | ++ | +++ | +++ | +++ |

[1] = Inoculum drop had $1.38 \times 10^5$ CFU organisms present. Divided by 5 ml equals $2.6 \times 10^4$ CFU/ml.
[2] = Inoculum drop had $2.78 \times 10^4$ CFU organisms present. Divided by 5 ml equals $3.56 \times 10^4$ CFU/ml.
[3] = Inoculum drop had $1.92 \times 10^5$ organisums present. Divided by 5 ml equals $3.84 \times 10^4$ CFU/ml.
TR = Treated.
UNTR = Untreated.

The treated bottle systems in Table V showed rapid reduction of the test organisms as evidenced by the absence of growth of the *S. aureus* in the 24 hour fluid sample, and the absence of growth on the tip or in the filter matrix. This is evidenced by the 2-2.5 log reduction of *E. coli* in the 24 hour fluid sample; the absence of growth at 14 days and absence of growth on the tip or in the filter matrix, and the 3 log reduction of *P. aeuroginosa* in the 24 hour fluid sample, absence of growth at 14 days, and absence of growth on the tip or in the filter matrix. All positive growth was confirmed to be the appropriate test organism. The criteria of the U.S. Pharmacopia "preservative challenge test" was met (3 log reduction in 14 days with no increase after 28 days), demonstrating that the system will preserve a packaged fluid from bacterial organisms sourced from outside.

It will be apparent from the foregoing that many other variations and modifications may be made in the compounds, compositions, and methods described herein without departing substantially from the essential features and concepts of the present invention. Accordingly, it should be clearly understood that the forms of the invention described herein are exemplary only and are not intended as limitations on the scope of the present invention.

That which is claimed is:

1. A method of dispensing an aqueous sterile fluid comprising storing a quantity of aqueous sterile fluid in a reservoir within a portable container having an outlet, arranging a porous filter medium within the container adjacent the outlet, and causing the aqueous sterile fluid to pass from the reservoir through the porous medium to the outlet, the porous medium having covalently bonded thereto an antimicrobially effective amount of an organosilicon quaternary ammonium compound, the organosilicon quaternary ammonium compound being an organosilane having the formula selected from the group consisting of consisting of

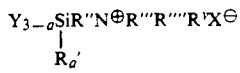

and

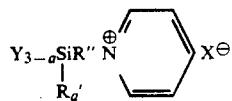

wherein, in each formula,

Y is R or RO where each R is an alkyl radical of 1 to 4 carbon atoms or hydrogen;

$a$ has a value of 0, 1, or 2;

R' is a methyl or ethyl radical;

R'' is an alkylene group of 1 to 4 carbon atoms;

R''', R'''' and $R^V$ are each independently selected from a group consisting of alkyl radicals of 1 to 18 carbon atoms, $-CH_2C_6H_5$, $-CH_2CH_2OH$, $-CH_2OH$, and $-(CH_2)_xNHC(O)R^{vi}$, wherein x has a value of from 2 to 10 and $R^{vi}$ is a perfluoroalkyl radical having from 1 to 12 carbon atoms; and X is chloride, bromide, fluoride, iodide, acetate or tosylate.

2. The method of claim 1 wherein the aqueous fluid is an ophthalmic saline solution which is free of preservatives.

3. The method of claim 2 wherein the wall of the portable container is constructed of a flexible material in order that the container wall may be squeezed to force the contents of the container from the reservoir through the porous filter medium and into the outlet.

4. The method of claim 3 in which the flexible material is selected from the group consisting of polyethylene, polypropylene, and acrylic polymers.

5. The method of claim 4 in which excess aqueous fluid in the outlet returns to the reservoir through the porous filter medium upon release of the container wall.

6. The method of claim 5 wherein the porous filter medium is constructed of a fiber strand selected from the group consisting of rayon, wool, nylon, cotton, silk, cellulose triacetate, polypropylene, polycarbonate, fiberglass, and polyester.

7. The method of claim 5 wherein the porous filter medium is a cellular foam material selected from the group consisting of polyurethane, polystyrene, polyvinyl chloride, polyethylene, and polypropylene.

8. The method of claim 5 wherein the porous filter medium is a high surface area particulate material selected from the group consisting of silica, ceramic, sintered metal, and sintered glass.

9. The method of claim 5 wherein the porous filter medium is constructed of a material selected from the group consisting of paper, mesh screen, and glass beads.

10. The method of claim 1 wherein the aqueous sterile fluid is selected from the group consisting of ophthalmic solutions, saline salt solutions, water delivered medicines, surgical irrigation fluids, water, milk, and emulsions.

11. The method of claim 1 in which the organosilane is bonded to the outer surfaces of the portable container.

12. The method of claim 11 in which the organosilane is bonded to the inner surfaces of the portable container.

13. The method of claim 12 in which the container reservoir includes a porous material therein and the porous material has the organosilane bonded thereto.

14. The method of claim 13 wherein the porous material having the organosilane bonded thereto is selected from the group consisting of beads and fibers.

15. The method of claim 14 wherein the fiber is a strand selected from the group consisting of rayon, wool, nylon, cotton, silk, cellulose, triacetate, polypropylene, polycarbonate, fiberglass, and polyester.

16. The method of claim 1 in which the organosilane is present in an amount in excess of about 0.5 percent by weight based on the total weight of the surface treated with the organosilane.

17. The method of claim 16 in which the amount of the organosilane is about 0.75 percent by weight.

18. The method of claim 1 in which the porous medium includes a wetting agent in addition to the organosilane, the wetting agent being selected from the group consisting of nonionic surfactants, cationic surfactants, and fluorocarbon surfactants.

19. The method of claim 1 wherein the organosilane is 3-(trimethoxysilyl) propyldimethyloctadecyl ammonium chloride of the formula

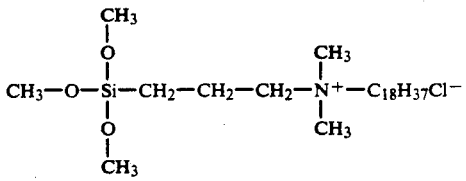

20. A method as claimed in claim 1 wherein the organosilicon compound has the formula

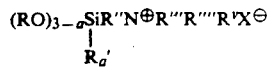

wherein each R is an alkyl radical of 1 to 4 carbon atoms or hydrogen; a has a value of 0, 1 or 2; R' is a methyl or ethyl radical; R" is an alkylene group of 1 to 4 carbon atoms; R''', R'''' and R$^v$ are each independently selected from a group consisting of alkyl radicals of 1 to 18 carbon atoms, —CH$_2$C$_6$H$_5$, —CH$_2$CH$_2$OH, —CH$_2$OH, and —(CH$_2$)$_x$NHC(O)R$^{vi}$, wherein x has a value of from 2 to 1 and R$^{vi}$ is a perfluoroalkyl radical having from 1 to 12 carbon atoms; X is chloride, bromide, fluoride, iodide, acetate or tosylate.

21. A method as claimed in claim 1 wherein the organosilicon compound has the formula

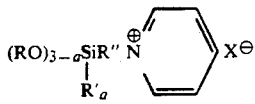

22. A device for dispensing an aqueous sterile fluid comprising a portable container having a reservoir in communication with an outlet, a porous filter medium within the container adjacent the outlet, the aqueous sterile fluid passing from the reservoir through the porous medium to the outlet, the pourous medium having covalently bonded thereto an antimicrobially effective amount of an organosilicon quaternary ammonium compound, the organosilicon quaternary ammonium compound being an organosilane having the forumla selected from the group consisting of

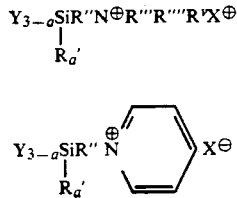

wherein, in each formula,
Y is R or RO where each R is an alkyl radical of 1 to 4 carbon atoms or hydrogen;
a has a value of 0, 1 or 2; R' is a methyl or ethyl radical;
R" is an alkylene group of 1 to 4 carbon atoms;
R''', R'''' and R$^v$ are each independently selected from a group consisting of alkyl radicals of 1 to 18 carbon atoms, —CH$_2$C$_6$H$_5$, —CH$_2$CH$_2$OH, =CH$_2$OH, and —(CH$_2$)$_x$NHC(O)R$^{vi}$, wherein x has a value of from 2 to 10 and R$^{vi}$ is a perfluoroalkyl radical having from 1 to 12 carbon atoms; and
X is chloride, bromide, fluoride, iodide, acetate or tosylate.

23. The device of claim 22 wherein the container includes a wall constructed of a flexible material in order that the container wall may be squeezed to force the contents of the container from the reservoir through the porous filter medium and into the outlet.

24. The device of claim 23 in which the flexible material is selected from the group consisting of polyethylene, polypropylene, and acrylic polymers.

25. The device of claim 24 in which excess aqueous fluid in the outlet returns to the reservoir through the porous filter medium upon release of the container wall.

26. The device of claim 25 wherein the porous filter medium is constructed of a fiber strand selected from the group consisting of rayon, wool, nylon, cotton, silk, cellulose triacetate, polypropylene, polycarbonate, fiberglass, and polyester.

27. The device of claim 25 wherein the porous filter medium is a cellular foam material selected from the group consisting of polyurethane, polystyrene, polyvinyl chloride, polyethylene, and polypropylene.

28. The device of claim 25 wherein the porous filter medium is a high surface area particulate material selected from the group consisting of silicon, ceramic, sintered metal, and sintered glass.

29. The device of claim 25 wherein the porous filter medium is constructed of a material selected from the group consisting of paper, mesh screen, and glass beads.

30. The device of claim 22 in which the organosilane is chemically bonded to the outer surfaces of the portable container.

31. The device of claim 30 in which the organosilane is chemically bonded to the inner surfaces of the portable container.

32. The device of claim 31 in which the container reservoir includes a porous material therein and the porous material has the organosilane chemically bonded thereto.

33. The device of claim 32 wherein the porous material having the organosilane chemically bonded thereto is selected from the group consisting of beads and fibers.

34. The device of claim 33 wherein the fiber is a strand selected from the group consisting of rayon, wool, nylon, cotton, silk, cellulose triacetate, polypropylene, polycarbonate, fiberglass, and polyester.

35. The method of claim 1 in which the organosilane is present in an amount in excess of about 0.5 percent by weight based on the total weight of the surface treated with the organosilane.

36. The device of claim 35 in which the amount of the organosilane is about 0.75 percent by weight.

37. The device of claim 22 in which the porous medium includes a wetting agent in addition to the organosilane, the wetting agent being selected from the group consisting of nonionic surfactants, cationic surfactants, and fluorocarbon surfactants.

38. The device of claim 22 wherein the organosilane is 3-(trimethoxysilyl) propyldimethyloctadecyl ammonium chloride of the formula

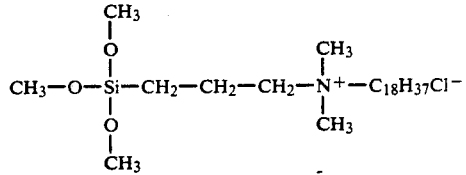

39. The device of claim 22 wherein the organosilicon compound has the formula

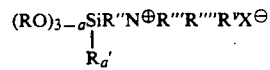

wherein each R is an alkyl radical of 1 to 4 carbon atoms or hydrogen; a has a value of 0, 1 or 2; R' is a methyl or ethyl radical; R" is an alkylene group of 1 to 4 carbon atoms; R''', R'''' and R$^v$ are each independently selected from a group consisting of alkyl radicals of 1 to 18 carbon atoms, —CH$_2$C$_6$H$_5$, —CH$_2$CH$_2$OH, —CH$_2$OH, and —(CH$_2$)$_x$NHC(O)R$^{vi}$, wherein x has a value of from 2 to 10 and R$^{vi}$ is a perfluoroalkyl radical having from 1 to 12 carbon atoms; X is chloride, bromide, fluoride, iodide, acetate or tosylate.
40. The device of claim 22 wherein the organosilicon compound has the formula
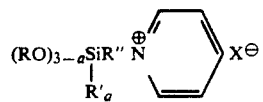
* * * * *